United States Patent [19]

Ross et al.

[11] Patent Number: 5,470,334
[45] Date of Patent: Nov. 28, 1995

[54] BIOABSORBABLE INTERFERENCE BONE FIXATION SCREW

[75] Inventors: Randall D. Ross; Kevin J. Bassetti, both of Largo, Fla.

[73] Assignee: Linvatec Corporation, Largo, Fla.

[21] Appl. No.: 902,352

[22] Filed: Jun. 22, 1992

Related U.S. Application Data

[63] Continuation of Ser. No. 664,679, Mar. 5, 1991, abandoned.

[51] Int. Cl.$^6$ .................................................. A61B 17/56
[52] U.S. Cl. ................... 606/72; 606/73; 606/77; 606/104
[58] Field of Search .................. 606/72, 73, 74, 606/75, 76, 77, 104; 81/460, 451, 436; 411/403, 404, 83, 358, 364, 400, 132; 433/174–176; 623/13

[56] References Cited

U.S. PATENT DOCUMENTS

| | | | |
|---|---|---|---|
| 2,397,216 | 6/1944 | Stellin . | |
| 2,445,525 | 7/1948 | Gulden | 411/404 |
| 2,445,978 | 5/1945 | Stellin . | |
| 3,122,963 | 8/1961 | Borgeson . | |
| 3,575,080 | 4/1971 | Hannay . | |
| 3,658,105 | 4/1972 | Burt et al. . | |
| 3,739,773 | 6/1973 | Schitt | 606/77 |
| 3,872,904 | 3/1975 | Barlow | 411/403 |
| 4,084,478 | 4/1978 | Simmons | 411/404 |
| 4,356,572 | 11/1982 | Guillemin et al. . | |
| 4,550,723 | 11/1985 | Belykh | 606/76 |
| 4,711,234 | 12/1987 | Vives | 606/76 |
| 4,754,749 | 7/1988 | Tsou | 411/83 |
| 4,927,421 | 5/1990 | Goble | 606/73 |
| 4,950,270 | 8/1990 | Bowman et al. . | |
| 5,019,080 | 5/1991 | Hemer . | |

FOREIGN PATENT DOCUMENTS

| | | | |
|---|---|---|---|
| 739089 | 1/1933 | France . | |
| WO09030 | 10/1989 | WIPO . | |
| 9008510 | 8/1990 | WIPO | 606/104 |

OTHER PUBLICATIONS

DePuy Data Sheet entitled "M. Kurosaka—The Critical Choice".

Primary Examiner—Michael A. Brown

[57] ABSTRACT

An interference bone fixation screw fabricated from bioabsorbable material includes a body having a proximal end, a distal end and a screw thread disposed therealong from the proximal end to the distal end. A drive recess is formed in the body to extend longitudinally from the proximal end toward the distal end for receiving a rotatable driver. The drive recess defines a plurality of radial force receiving surfaces for receiving concentric forces from the driver applied perpendicularly to the force receiving surfaces.

31 Claims, 1 Drawing Sheet

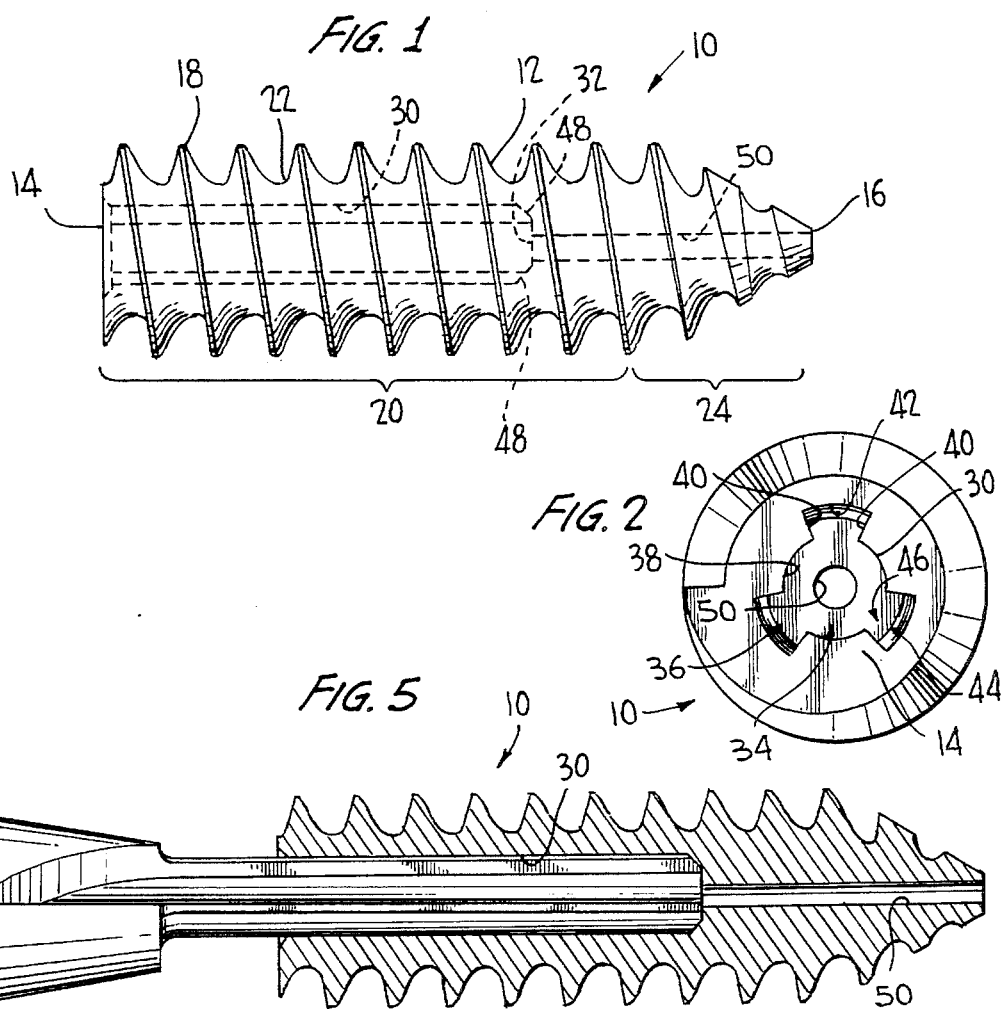
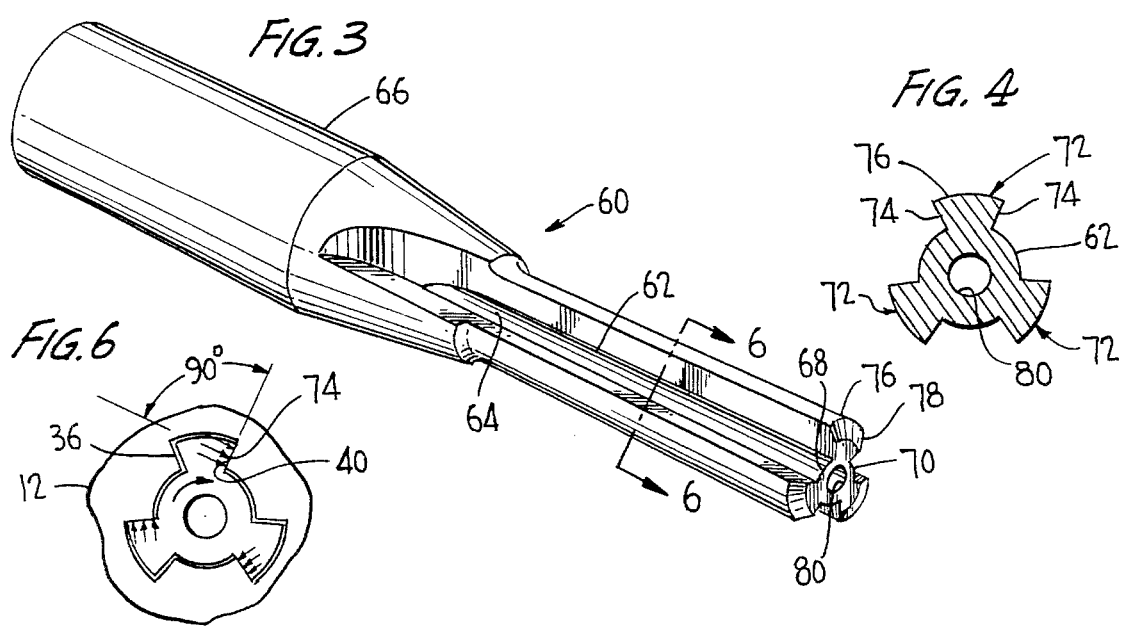

BIOABSORBABLE INTERFERENCE BONE FIXATION SCREW

This is a continuation application of application Ser. No. 07/664,679, filed Mar. 5, 1991, now abandoned.

BACKGROUND OF THE INVENTION

1. Field Of The Invention

The present invention relates to surgical screws for fixation in bone and, more specifically, to bioabsorbable interference bone screws particularly useful in securing a ligament in a bone tunnel.

2. Description Of The Prior Art

Graft and prosthetic ligaments are utilized to surgically repair and/or replace ligaments damaged by injury or disease. Surgical procedures to repair and/or replace ligaments generally involve forming a tunnel in bone, positioning a graft or prosthetic ligament in the bone tunnel, and anchoring the ends. Various devices are typically employed to secure the bone blocks the ligament in the bone tunnel, including buttons, staples, expanding cones, unicortical screw posts, as well as interference screws. When interference screws are used, the screws are inserted into the bone tunnel to engage the tunnel wall and bone blocks at the ends of the ligament and, thus, provide an endosteum or endosteal fixation therebetween.

Surgical bone screws for fixation in bone and for anchoring ligaments to bone are typically fabricated from medically approved metallic materials that are not naturally absorbed by the body. An illustrative metallic bone screw is the M. Kurosaka™ bone screw manufactured by DePuy, a division of Boehringer Mannheim Corporation, and a further example of a metallic bone screw is shown in U.S. Pat. No. 4,754,749 to Tsou. Most metallic bone screws include a threaded shank joined to an enlarged head having a transverse slot or hexagonal socket formed therein to engage, respectively, a similarly configured, single blade or hexagonal rotatable driver for turning the screw into a bone. The enlarged heads on such screws can protrude from the bone and can cause chronic irritation and inflammation of surrounding body tissue. Metallic bone screws that do not have enlarged heads possess disadvantages because mismatch between screw length and the length of the ligament bone block can result in the screw being inserted too far, or not being inserted to its full length, in the bone tunnel. In anterior cruciate ligament repair and reconstruction, insertion of the screw too far can produce intraarticular penetration, and failure to insert the screw its full length can irritate adjacent soft tissue. Additionally, placement of screws in bone tunnels formed in movable joints can, in certain instances, cause abrading of ligaments during normal motion of the joint. Furthermore, bone screws occasionally back out after insertion; and, when this occurs, the bone screw can protrude into surrounding tissue and cause discomfort. Because metallic bone screws are not assimilated by the body, additional surgical procedures may be required to remove problematic bone screws once the fixated bone and/or tissue has healed.

Biodegradable bone screws have been proposed, as exemplified in U.S. Pat. No. 4,356,572 to Guillemin and International Application PCT/EP 89/00344, and as alluded to in U.S. Pat. No. 4,927,421 to Goble et al. Bioabsorbable bone screws possess the advantage of being naturally degradable by the body; and, therefore, contact with surrounding tissue after insertion does not necessitate surgical intervention because the screw will be completely absorbed by the body once the bone and/or tissue has healed. However, conventional bioabsorbable bone screws present numerous difficulties due to bioabsorbable materials being considerably softer than metallic compositions. In particular, bone screws made from bioabsorbable materials are susceptible to deformation and deflection when subjected to forces required to drive the screw into relatively hard tissue, such as bone, and the transverse slot and hexagonal socket typically provided in bone screws as drive recesses for receiving standard, similarly configured, rotatable drivers are unsuitable for bone screws fabricated of bioabsorbable material. The high torque that must be applied to bone screws by a driver to produce rotation of the screw in bone can cause shear deformation of the relatively soft bioabsorbable material, and the surfaces of the drive recesses can be sheared, or stripped, by the drivers. Additionally, single blade and hexagonal drivers tend to force the walls of the drive recesses outwardly when rotated therein producing outward expansion, or "mushrooming" of bioabsorbable screws. Furthermore, some drive recesses extend the entire length of the bone screw, and these drive recesses require that a significant quantity of material be removed from the bone screw resulting in a reduction in strength of the bone screw and impairing the overall resistance of the screw to deformation and damage when being driven into bone. For similar reasons, bioabsorbable bone screws are generally limited to use in open surgery, as opposed to closed, or endoscopic, surgery, because it is advantageous in endoscopic techniques for the screws to be cannulated, i.e. include a central longitudinal bore, for insertion along a guide wire. Formation of the central bore involves removing additional quantities of material from the screw and, therefore, structurally weakens bioabsorbable screws.

Alternative drive recesses, such as those defining multiple, radially oriented prongs for receiving similarly configured, multi-pronged drivers have been proposed for metallic screws, and illustrative drive arrangements are shown in U.S. Pat. Nos. 4,084,478 to Simmons; 3,872,904 to Barlow; 3,658,105 to Burt et al; 3,575,080 to Henney; 3,122,963 to Borgeson; 2,445,978 to Stellin; 2,445,525 to Gulden and 2,397,216 to Stellin. These drive recesses are formed in enlarged heads on metallic industrial screws, and typically taper longitudinally to a narrow end for engaging a similarly tapered driver. Multi-pronged drive recesses designed for metallic screws generally cannot be employed successfully in bioabsorbable bone screws because the forces applied by compatible multi-pronged drivers to such drive recesses include outwardly directed force components that cause outward expansion, or "mushrooming", in bioabsorbable bone screws. Furthermore, the walls defining multi-pronged drive recesses are typically configured to permit outward expansion of the screw material separating the radial prongs of the drive recess when the associated driver imposes force on the walls. Although this configuration is acceptable for metallic screws, it further promotes "mushrooming" in bioabsorbable bone screws due to the inherent relative softness of bioabsorbable materials. Conventional multi-pronged drivers also produce shear on the walls of corresponding drive recesses; and, when utilized in bioabsorbable bone screws, the walls can be sheared off, or stripped, by the drivers. Furthermore, many conventional multi-pronged drive recesses have only a small quantity of screw material separating the radial prongs of the drive recesses, and bioabsorbable bone screws having these types of drive recesses would be particularly vulnerable to shear deformation and could not withstand high drive forces.

Additionally, the longitudinal taper in conventional multi-pronged drive recesses results in high concentrations of drive forces being applied by the drivers at the narrow end of the drive recesses where there is relatively less screw material to resist deformation, and bioabsorbable screws having tapered drive recesses are likely to experience significant deformation when driven into bone.

SUMMARY OF THE INVENTION

Accordingly, it is a primary object of the present invention to overcome the above mentioned disadvantages associated with prior art metal and bioabsorbable bone screws.

Another object of the invention is to eliminate radial deformation in a bioabsorbable bone screw when it is driven into bone.

It is also an object of the invention to eliminate shear deformation in a bioabsorbable bone screw when it is driven into bone.

Moreover, it is an object of the invention to prevent outward expansion, or "mushrooming", of a bioabsorbable bone screw when it is driven into bone.

A further object of the invention is to provide a bioabsorbable bone screw capable of withstanding high drive forces when driven into bone.

Another object of the invention is to provide a bioabsorbable bone screw having a multi-lobed drive recess receiving a multi-lobed driver that applies concentric forces to walls of the drive recess in a direction perpendicular to such walls.

A still further object of the invention is to provide a bioabsorable bone screw including a drive recess having radially oriented force receiving walls for receiving forces from a driver applied perpendicularly to such walls.

Some of the advantages of the bioabsorbable interference bone fixation screw according to the present invention over the prior art are that the bone screw is naturally degraded and absorbed by the body upon completion of healing of the fixated bone and/or tissue, presents no exterior enlargements that might protrude into bodily tissue, is self-tapping and is suitable for use in closed, or endoscopic, surgery as well as in open surgery.

These and other objects, attributes and benefits are achieved with the bioabsorbable interference bone fixation screw of the present invention as characterized by a body having a proximal end, a conically tapered distal end and a helical screw thread disposed on the body from the proximal end to the distal end and having a major diameter that defines the major diameter for the bone screw. A drive recess for engaging a rotatable driver is formed in the body to extend longitudinally from the proximal end toward the distal end. The drive recess includes a cylindrical cavity disposed concentrically in the body, and a plurality of lobe openings positioned radially around the cavity in communication therewith and extending longitudinally therealong. Each of the lobe openings is defined by a pair of side walls in radial alignment with the central longitudinal axis of the body, and an arcuate outer wall joining the side walls, such that the lobe openings are wider at the arcuate outer walls and narrower at the cylindrical cavity. A central longitudinal guide bore is formed in the body to extend longitudinally from the drive recess to the distal end for guiding the screw on a guide wire. A driver configured to be matingly received in the drive recess includes a shaft and a plurality of lobes having side walls extending radially outwardly from the shaft for applying concentric forces to the side walls of the drive recess in a direction perpendicular to such side walls.

Other objects and advantages of the present invention will become apparent from the following description of the preferred embodiment taken in conjunction with the accompanying drawings wherein like parts in each of the several figures are identified by the same reference characters.

BRIEF DESCRIPTION OF THE DRAWINGS

FIG. 1 is a side view of the bioabsorbable interference bone fixation screw according to the present invention.

FIG. 2 is a proximal end view of the bioabsorbable interference bone fixation screw of FIG. 1.

FIG. 3 is a perspective view of a driver for rotating the bioabsorbable interference bone fixation screw of FIG. 1.

FIG. 4 is a cross-sectional view of the driver taken along line 6—6 of FIG. 3.

FIG. 5 is a broken, longitudinal sectional view of the driver inserted in the bone screw of FIG. 1.

FIG. 6 is a broken, sectional view showing the bone screw of FIG. 1 being driven by the driver.

DESCRIPTION OF THE PREFERRED EMBODIMENT

Referring to FIGS. 1 and 2, the bone screw 10 according to the present invention includes a longitudinally elongated cylindrical body 12 having a proximal end 14, a distal end 16 and a helical screw thread 18 disposed externally on body 12 from proximal end 14 to distal end 16. Thread 18 includes a proximal thread section 20 extending longitudinally from the proximal end 14 in the direction of the distal end 16 and a conically tapered distal thread section 24 extending longitudinally from the proximal thread section 20 to the distal end 16. The threads of proximal thread section 20 are of uniform pitch and like-handed; that is, they extend in the same angular direction about the screw. The major diameter (i.e., the diameter of the crests) of the threads in proximal thread section 20 defines the major diameter for the screw, and a cylindrical surface 22 on body 12 defines the minor diameter for proximal thread section 20. Distal thread section 24 carries a thread having a major diameter that is less than the major diameter of the threads in proximal thread section 20. The thread for distal thread section 24 tapers conically from the proximal thread section 20 to the distal end 16 in a spiral configuration, and the pitch of this thread is greater than the pitch of the threads in the proximal thread section 20.

A drive recess 30 for receiving a rotatable driver is formed in body 12 to extend longitudinally from proximal end 14 in the direction of distal end 16 to an end wall 32 disposed perpendicular to the central longitudinal axis of body 12. As best shown in FIG. 2, drive recess 30 includes a cylindrical cavity 34 formed concentrically in body 12 to extend longitudinally from proximal end 14 to end wall 32 and three equally spaced lobe openings or chambers 36 radially disposed around cavity 34 in communication therewith and extending longitudinally therealong to end wall 32. Cavity 34 is defined by three inner arcuate walls 38 positioned between lobe openings 36 and disposed a constant radial distance from the central longitudinal axis of body 12. Each lobe opening 36 is defined by a pair of spaced, planar side walls 40 and an outer arcuate wall 42 joining opposing side walls 40. Outer arcuate walls 42 are disposed a constant radial distance from the central longitudinal axis of body 12, and this radial distance is greater than the radial distance for inner arcuate walls 38. Side walls 40 extend radially outwardly from inner arcuate walls 38 and are positioned in radial alignment with the central longitudinal axis of body 12, such that lobe openings 36 taper inwardly from an outer end 44 defined by outer arcuate walls 42 to a mouth or inner end 46 communicating with cavity 34. Outer arcuate walls 42 are joined to end wall 32 by inwardly curved walls 48, such that the cross-section of drive recess 30 is constant through a substantial portion of its length. A central, longitudinal guide bore or cannulation 50 is disposed concentrically within body 12 in communication with drive recess 30 and extends longitudinally from end wall 32 to distal end 16.

Preferably, the minor diameter for the proximal thread section 20 defined by the surface 22 is 55% to 75% the major diameter for the screw; the thread 18 is configured approximately in accordance with ISO 5835/1; the length of the drive recess 30 from proximal end 14 to end wall 32 is approximately 48% to 95% the overall length of body 12 measured from proximal end 14 to distal end 16; the inner arcuate walls 38 of the cavity 34 define arcs of a circle having a diameter that is in the range of 20% to 70% the minor diameter of the proximal thread section 20; the outer arcuate walls 42 of the lobe openings 36 define arcs subtending approximately 50° along a circle having a diameter that is approximately 78% the minor diameter of proximal thread section 20 and these arcs are shorter in length than the arcs defined by inner arcuate walls 38.

The relative proportions of the bone screw produce numerous structural and functional advantages. The relatively large minor diameter for the thread 18 in the proximal thread section 20 increases the quantity of screw material surrounding the drive recess 30 and, therefore, the strength of the bone screw in resisting shear and radial deformation when being rotated by a driver received in the drive recess. The size of the minor diameter for the proximal thread section 20 relative to the major diameter for the bone screw increases the overall strength of the body 12 yet provides thread 18 with sufficient depth to insure proper fixation in bone. The conical taper for the distal thread section 24 and the spiral configuration and relatively greater pitch of the thread in the distal thread section assists advancement of the bone screw and eliminates the need for a tapping procedure. The length of the drive recess 30 relative to the overall length of the body 12 and to the minor diameter for the proximal thread section 20 allows drive forces to be distributed through body 12 and increases the magnitude of force that the bone screw can withstand. Furthermore, the length of the drive recess 30 is selected to limit the quantity of material removed from the screw and maintain structural integrity around the cannulation 76. Additionally, drive recess 30 distributes drive forces equally throughout its length due to the crosssection of the drive recess being constant through a substantial portion of its length. The diameters of the circles defined by the inner arcuate walls 38 and the outer arcuate walls 42 of the drive recess 30 further insure that a quantity of screw material sufficient to withstand drive forces surrounds the drive recess 30, and the length of the arcs defined by the outer arcuate walls 42 provides relatively large quantities of screw material between the lobe openings 36.

Bone screw 10 is fabricated entirely from a bioabsorbable or biodegradable polymer or copolymer having an absorption or degradation time selected in accordance with the anticipated healing time for the fixated tissue. Table I set forth below lists polymers (and copolymers and terpolymers thereof) suitable for bone screw 10, and these polymers are all biodegradable into water-soluble, non-toxic materials that are safely eliminated by the body. Although the illustrative polymers are normally linear, suitable cross linked resins can be prepared therefrom.

TABLE I

| Polymer |
|---|
| Polycaprolactone |
| Poly (L-lactide) |
| Poly (DL-lactide) |
| Polyglycolide |
| 95:5 Poly (DL-lactide-co-glycolide) |
| 90:10 Poly (DL-lactide-co-glycolide) |
| 85:15 Poly (DL-lactide-co-glycolide) |
| 75:25 Poly (DL-lactide-co-glycolide) |
| 50:50 Poly (DL-lactide-co-glycolide) |
| 90:10 Poly (DL-lactide-co-caprolactone) |
| 75:25 Poly (DL-lactide-co-caprolactone) |
| 50:50 Poly (DL-lactide-co-caprolactone) |

A preferred material for bone screw 10 is Poly (L-Lactide), and the preferred chemical specifications for raw poly-lactide acid employed for bone screw 10 are set forth below in Table II.

TABLE II

| Raw Poly-Lactic Acid |
|---|
| Residual Tin (Stannous octoate): Less than 200 ppm |
| Residual Metals (FE, Cr, Ni, Pb): Less than 50 ppm each |
| Residual Lactide Dimer: Less than 1% |
| Intrinsic Viscosity: 6.5–8.5 dL/g in chloroform at 25° C. |

Bone screw 10 is preferably formed by an injection molding process, and the preferred characteristics of the bone screw thusly formed are set forth below in Table III.

TABLE III

| Bone Screw |
|---|
| Ultimate Tensile Strength: 9,000–15,000 psi |
| Tensile Modulus: 330,000–530,000 psi |
| Maximum Bending Strength: 12,900–20,900 psi |
| Bending Modulus: 417,000–617,000 psi |
| Intrinsic Viscosity: 2.0–4.5 dL/g in chloroform at 25° C. |

A rotatable driver 60 for engagement in drive recess 30 is shown in FIGS. 3 and 4 and includes a longitudinally elongated, cylindrical shaft 62 having a proximal end 64 joined to a handle 66, a distal end 68 defining a distal end wall 70 disposed perpendicular to the central longitudinal axis of shaft 62, and three lobes 72 disposed radially on shaft 62 to extend longitudinally from proximal end 64 to distal end 68. Lobes 72 each include spaced, planar side walls 74 extending radially outwardly with respect to the central longitudinal axis of shaft 62 and an outer arcuate wall 76 joining side walls 74, such that side walls 74 are closer together at shaft 62 and farther apart at outer arcuate wall 76. Outer arcuate walls 76 are joined to distal end wall 70 by inwardly curved walls 78, such that the cross-sections of lobes 72 and shaft 62 are constant through a substantial portion of their length. A longitudinal guide bore 80 is formed concentrically in shaft 62 and handle 66 to extend the entire length of shaft 62 and handle 66. As shown in FIGS. 5 and 6, shaft 62 is sized to be matingly received in cavity 34 of drive recess 30, and lobes 72 are sized to be matingly received in lobe openings 36 of drive recess 30.

In operation, bone screw 10 can be employed in ligament repair and/or reconstruction surgery to attach a bone block on a ligament to the wall of a bone tunnel. For example, for ligament fixation in endoscopic intraarticular replacement of the anterior cruciate ligament of the knee, appropriate portals are made leading to the knee joint for insertion of an arthroscope and other instruments, and bone tunnels are formed, respectively, in the proximal tibia and distal femur. A ligament, either graft or prosthetic, having bone blocks at its ends is passed through the femoral tunnel, across the joint, and through the tibial tunnel to position a bone block in the femoral and tibial tunnels. Sutures carried by the bone blocks permit the ligament to be placed in tension. Bone screw 10 is inserted via guide bore 50 over a guide wire positioned in the femoral bone tunnel between the bone block positioned therein and the tunnel wall. Driver 60 is placed over the guide wire via guide bore 80 and is guided into mating engagement with drive recess 30 as shown in FIG. 5. Driver 60 is rotated to drive bone screw 10 into interference fit between the bone block and the wall of the femoral bone tunnel. With the ligament held in tension, a second bone screw 10 is inserted to secure the remaining bone block with respect to the wall of the tibial bone tunnel.

As shown in FIG. 6, when driver 60 is rotated, the leading radial side walls 74 of lobes 72 apply rotation forces equally against corresponding radial side walls 40 of lobe openings 36, and these rotational forces are concentric to the central longitudinal axis of body 12. The forces applied by side walls 74 to side walls 40 are directed perpendicularly, and not outwardly, against side walls 40. Therefore, forces are applied by driver 60 only in the direction needed to drive screw 10, and extraneous forces that would otherwise produce distortion or outward expansion of screw 10 are eliminated. Because lobe openings 36 taper inwardly from outer ends 44 to mouths 46, the screw material separating lobe openings 36 is restricted, or confined, against outward expansion when the leading side walls 74 of driver 60 are forced against corresponding side walls 40.

Having described a preferred embodiment of a new and improved bioabsorbable interference bone fixation screw, it is believed that other modifications, variations and changes will be suggested to those skilled in the art in view of the teachings set forth herein. It is therefore to be understood that all such variations, modifications and changes are believed to fall within the scope of the present invention as defined by the appended claims.

What is claimed is:

1. An interference bone fixation screw to be rotated by a driver comprising
   a body having a proximal end, a distal end, a length between said proximal and distal ends and a longitudinal axis;
   thread means for engaging bone disposed on said body from said proximal end to said distal end; and
   drive recess means disposed in said proximal end of said body including a plurality of equally spaced lobe openings having force receiving surfaces in radial alignment with said longitudinal axis for receiving rotational forces from the driver, said force receiving surfaces extending longitudinally within said body along a substantial portion of said length,
   said interference bone fixation screw being made of bioabsorbable material in its entirety.

2. An interference bone fixation screw as recited in claim 1 wherein said drive recess means further includes a cylindrical cavity disposed concentrically in said body and said force receiving surfaces are positioned radially around said cavity.

3. An interference bone fixation screw as recited in claim 2 further including a longitudinal guide bore disposed concentrically in said body to extend longitudinally from said cavity to said distal end.

4. An interference bone fixation screw as recited in claim 3 wherein said drive recess means includes an end wall disposed in said body perpendicular to said longitudinal axis and said force receiving surfaces extend longitudinally in said body from said proximal end to said end wall.

5. An interference bone fixation screw as recited in claim 4 wherein said thread means includes a helical screw thread.

6. An interference bone fixation screw as recited in claim 5 wherein said helical screw thread defines a major diameter and said body defines a minor diameter along said helical screw thread.

7. An interference bone fixation screw as recited in claim 6 wherein said minor diameter is approximately 55% to 75% said major diameter.

8. An interference bone fixation screw as recited in claim 7 wherein said helical screw thread is of uniform pitch.

9. An interference bone fixation screw as recited in claim 8 wherein said screw thread further includes a spiral screw thread extending longitudinally from said helical screw thread to said distal end.

10. An interference bone fixation screw as recited in claim 9 wherein said spiral screw thread has a pitch and said spiral screw thread pitch is greater than said helical screw thread pitch.

11. An interference bone fixation screw as recited in claim 10 wherein said interference bone fixation screw is made entirely of Poly (L-Lactide).

12. An interference bone fixation screw as recited in claim 1 wherein said force receiving surfaces extend within said body from 48% to 95% of said length.

13. An interference bone fixation screw to be rotated by a driver comprising
   a cylindrical body having a proximal end, a distal end, a length between said proximal and distal ends and a longitudinal axis;
   a screw thread disposed on said body to extend longitudinally therealong; and
   drive recess means disposed in said proximal end of said body including a plurality of equally spaced lobe openings extending longitudinally within said body along a substantial portion of said length,
   said lobe openings having outer ends disposed a first radial distance from said longitudinal axis and inner ends disposed a second radial distance from said longitudinal axis less than said first radial distance,
   said lobe openings tapering inwardly from said outer ends to said inner ends to define planar force receiving walls between said outer ends and said inner ends for receiving rotational forces from the driver,
   said interference bone fixation screw being made entirely of bioabsorbable material.

14. An interference bone fixation screw as recited in claim 13 wherein said drive recess means includes a cylindrical cavity disposed concentrically in said proximal end of said body and said inner ends of said lobe openings communicate with said cylindrical cavity.

15. An interference bone fixation screw as recited in claim 14 wherein said cylindrical cavity is defined by a plurality of inner concave arcuate walls positioned, respectively, between said inner ends of said lobe openings.

16. An interference bone fixation screw as recited in claim 15 wherein said outer ends of said lobe openings are defined by outer concave arcuate walls joining said force receiving 17. An interference bone fixation screw as recited in claim 16 wherein said outer arcuate walls define arcs of a circle, said inner arcuate walls define arcs of a circle and said arcs defined by said inner arcuate walls are longer than said arcs defined by said outer arcuate walls.

18. An interference bone fixation screw as recited in claim 17 wherein said screw thread defines a major diameter and said body defines a minor diameter extending longitudinally from said proximal end toward said distal end.

19. An interference bone fixation screw as recited in claim 18 wherein the diameter of said circle defined by said outer arcuate walls is approximately 78% said minor diameter.

20. An interference bone fixation screw as recited in claim 19 wherein the diameter of said circle defined by said inner arcuate walls is 20% to 70% of said minor diameter.

21. An interference bone fixation screw as recited in claim 20 wherein said arcs defined by said outer arcuate walls subtend approximately 50°.

22. An interference bone fixation screw as recited in claim 21 wherein there are three of said lobe openings.

23. An interference bone fixation screw as recited in claim 13 wherein said force receiving surfaces extend within said body from 48% to 95% of said length.

24. An interference bone fixation screw to be rotated by a driver comprising a cylindrical body having a proximal end, a distal end a length between said proximal and distal ends and a longitudinal axis;

a screw thread disposed on said body to extend longitudinally from said proximal end to said distal end; and a drive recess in said proximal end of said body for matingly receiving the driver including a plurality of equally spaced lobe openings extending longitudinally within said body along a substantial portion of said length, each of said lob openings being defined by a pair of spaced side walls extending radially outwardly with respect to said longitudinal axis for receiving rotational forces from the driver applied perpendicular to said side walls, said interference bone fixation screw being made of bioabsorbable material in its entirety.

25. An interference bone fixation screw as recited in claim 24 wherein the cross-section of the drive recess is constant through a substantial portion of said longitudinal length of said drive recess.

26. An interference bone fixation screw as recited in claim 25 wherein the longitudinal length of said drive recess is approximately 48% to 95% said length of said body.

27. In combination, an interference bone fixation screw comprising a cylindrical body having a proximal end, a distal end and a longitudinal axis, thread means disposed on said body for engaging bone and drive recess means in said proximal end of said body including a cylindrical cavity disposed concentrically in said body and extending along a length thereof and a plurality of lobe openings disposed around said cavity in communication therewith along the length thereof, each of said lobe openings being defined by force receiving walls extending radially outwardly from said cavity, said force receiving surfaces extending longitudinally within said body along a substantial portion of said length said interference bone fixation screw being fabricated entirely of bioabsorbable material; and a driver for rotating said screw and having a configuration mating with said drive recess means, said driver including cylindrical shaft means for being received in said cavity and a plurality of lobe means having force transmitting walls extending radially outwardly from said shaft means for applying forces to said force receiving walls when said driver is rotated.

28. A combination as recited in claim 27 wherein said drive recess means includes an end wall disposed in said body perpendicular to said longitudinal axis, said cavity extends longitudinally from said proximal end to said end wall and said shaft means includes an end surface on said driver for engaging said end wall.

29. A combination as recited in claim 28 and further including a guide bore in said body extending longitudinally from said drive recess end wall to said distal end and a guide passage in said shaft means of said driver aligned with said guide bore when said shaft means is received in said cavity.

30. A driver for rotating a bioabsorbable bone screw having a body with a proximal end and a drive recess extending longitudinally within a substantial length of the body, said driver comprising a cylindrical shaft and a plurality of lobes extending from said shaft along a substantial length thereof, each of said lobes carrying radially oriented, spaced, planar side walls which diverge outwardly from the axis of said shaft and are joined by an arcuate outer wall forming part of a cylinder concentric with said shaft for engaging walls of the drive recess of the screw whereby said driver engages the screw along a substantial length of the screw body for rotating the screw.

31. A driver for rotating a bioabsorbable bone screw as recited in claim 30 wherein said shaft terminates at a distal end wall disposed perpendicular to the longitudinal axis of the shaft and said outer arcuate walls of said lobes terminate at inwardly curved walls joining said distal end wall.

\* \* \* \* \*